United States Patent
Hollingsworth et al.

(10) Patent No.: US 6,612,184 B1
(45) Date of Patent: Sep. 2, 2003

(54) METHOD AND APPARATUS FOR TESTING BONDED TUBULAR JOINTS

(75) Inventors: Jimmy Lawrence Hollingsworth, Langenhagen (DE); Bernd-Georg Pietras, Wedemark (DE)

(73) Assignee: Shell Research Limited, London ( * ) Notice: Subject to any disclaimer, the term of this patent is extended or adjusted under 35 U.S.C. 154(b) by 0 days.

(21) Appl. No.: 09/508,329

(22) PCT Filed: Sep. 8, 1998

(86) PCT No.: PCT/EP98/05746
§ 371 (c)(1),
(2), (4) Date: Mar. 9, 2000

(87) PCT Pub. No.: WO99/13314
PCT Pub. Date: Mar. 18, 1999

(30) Foreign Application Priority Data

Sep. 9, 1997 (GB) .............................................. 9719124

(51) Int. Cl.[7] .............................................. G01N 3/08
(52) U.S. Cl. .............................. 73/827; 73/846; 73/850
(58) Field of Search .......................... 73/827, 846, 850, 73/803, 794, 795, 800, 808, 814, 853

(56) References Cited

U.S. PATENT DOCUMENTS

| | | | | |
|---|---|---|---|---|
| 3,797,304 A | * | 3/1974 | Klinger | 73/99 |
| 4,517,843 A | * | 5/1985 | Leger | 73/847 |
| 4,836,031 A | * | 6/1989 | Jatho et al. | 73/800 |
| RE34,686 E | * | 8/1994 | Coyle et al. | 73/761 |

FOREIGN PATENT DOCUMENTS

JP   03061834 A   *   3/1991   ............ G01N/3/34

OTHER PUBLICATIONS

Academic Press Dictionary of Science and Technology. Hardcount.http://www.harcourt.com/dictionary/.*

* cited by examiner

Primary Examiner—Edward Lefkowitz
Assistant Examiner—Lilybett Martir

(57) ABSTRACT

There is provided a method of testing a joint formed by bonding of two tubulars, which method comprises the steps of holding a first tubular; applying a force to displace a second tubular relative to the first tubular; and removing the force. The final position of the second tubular is then compared with the position which it occupied prior to the application of the force by means of a sensor mounted remotely from the second tubular.

10 Claims, 5 Drawing Sheets

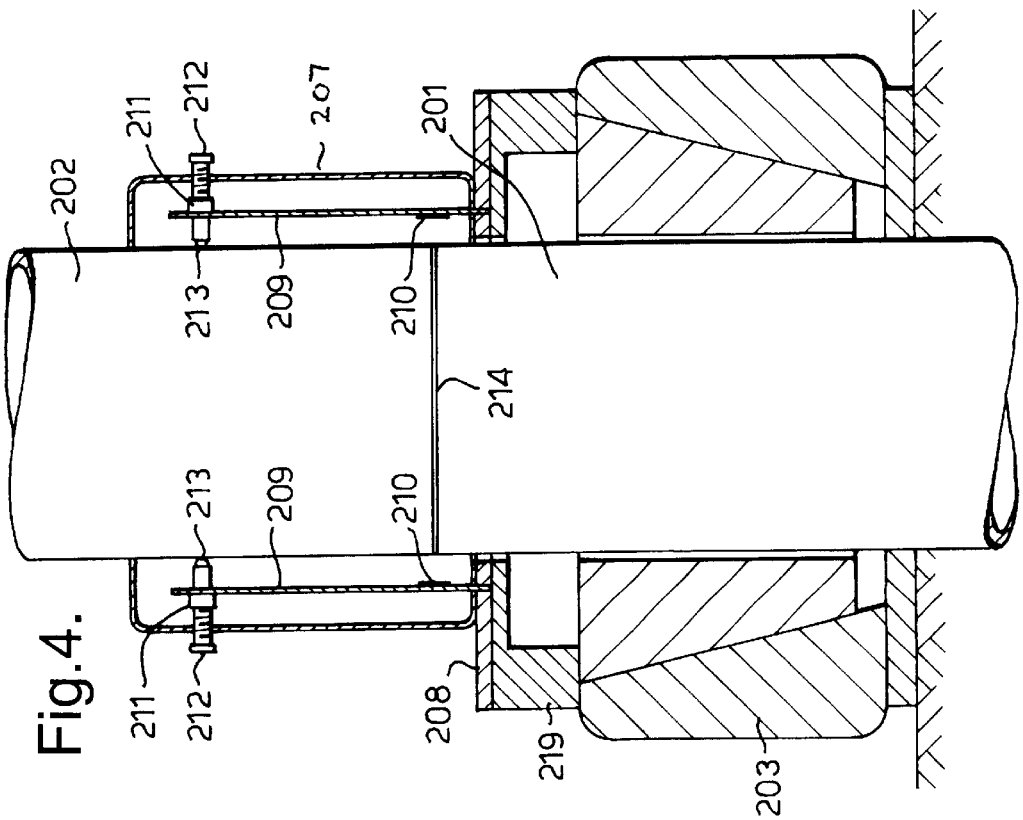
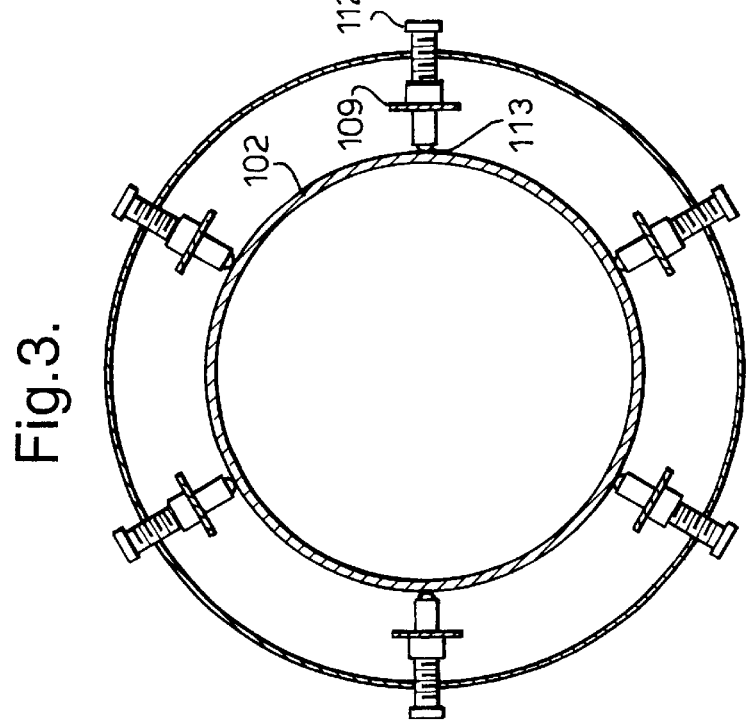

METHOD AND APPARATUS FOR TESTING BONDED TUBULAR JOINTS

BACKGROUND OF THE INVENTION

This invention relates to a method of testing joints formed by bonding of tubulars and to an apparatus for carrying out such method.

Conventionally, tubulars used in the construction, maintenance and repair of oil and gas wells are joined by mechanical couplings. Typically, one tubular is provided with a threaded socket which receives a threaded pin on the next tubular. The mechanical characteristics of the couplings are well known and although it is not unusual to test the joints to make sure they are not leaking it is not customary to check them for their load bearing ability.

While mechanical couplings are quite adequate for many situations, they do have certain disadvantages. In particular, they are prone to failure in wells which contain highly corrosive vapors. In such wells it is not uncommon for the entire string to have to be replaced every few years. However, in the absence of such mechanical couplings it is widely believed that the tubular itself could be expected to have a working life of about 25 years.

Welding has been attempted as an alternative to mechanical couplings. However, this is difficult to carry out in the hazardous environment present at the top of an oil or gas well. Furthermore, normal welding generally creates metallurgical discontinuities which provide areas which are also susceptible to corrosion.

Amorphous bonding is a technique which has been successfully used for joining metal parts, particularly in the automotive industry, for several years. In general terms the surfaces to be connected are ground until they are exactly parallel. Next a thin film of a special alloy is placed between the surfaces. The pieces are then pressed towards one another and heat applied for several minutes. This process results in a finished component which has a nearly homogeneous metallurgical structure. It will be appreciated that it would be highly desirable to use amorphous bonding for the connection of tubulars for use in oil wells.

It is known from U.S. Pat. No. 2,761,310 to use a device for fatigue testing a welded tube, wherein the tube is heated and pressurized and one end of the tube is rotated so that the tube is twisted in opposite directions. U.S. Pat. No. 3,845,657 discloses the use of strain gages for detecting cracks in the welds of pipes.

SUMMARY OF THE INVENTION

The present invention is concerned with an improved technique for testing the joint after it has been made by an amorphous or other bonding process. The technique could also be used for testing joints made by other bonding processes than amorphous bonding, for example by welding or by adhesive.

According to the present invention there is provided a method of testing a joint formed by bonding of two tubulars, which method comprises the steps of:

a) providing a first tubular and a second tubular, wherein an end of the first tubular is bonded to an end of the second tubular to form a joint therein between;

b) holding said first tubular;

c) applying a force to displace said second tubular relative to said first tubular;

d) removing said force; and e) comparing the final position of said second tubular with the position which it occupied prior to step (c) by means of a sensor mounted remote from said joint.

The present invention also provides an apparatus for testing a joint formed by bonding of two tubulars which apparatus comprises:

a) a fixing device to hold a first tubular;

b) a head to grip a second tubular, an end of second tubular connected to an end of said first tubular to form a joint;

c) a sensor remote to said joint, which sensor is responsive to the position of said second tubular;

d) means to move said head to displace said second tubular relative to said first tubular; and e) means to allow said head to move to a position dictated by said second tubular.

BRIEF DESCRIPTION OF THE DRAWINGS

For a better understanding of the present invention reference will now be made, by way of example, with reference to the accompanying drawings, in which:

FIG. 3 is a simplified view taken on line III–III of FIG. 1;

FIG. 4 is a scrap view of an alternative sensing apparatus;

DETAILED DESCRIPTION OF PREFERRED EMBODIMENTS

Figure 1:
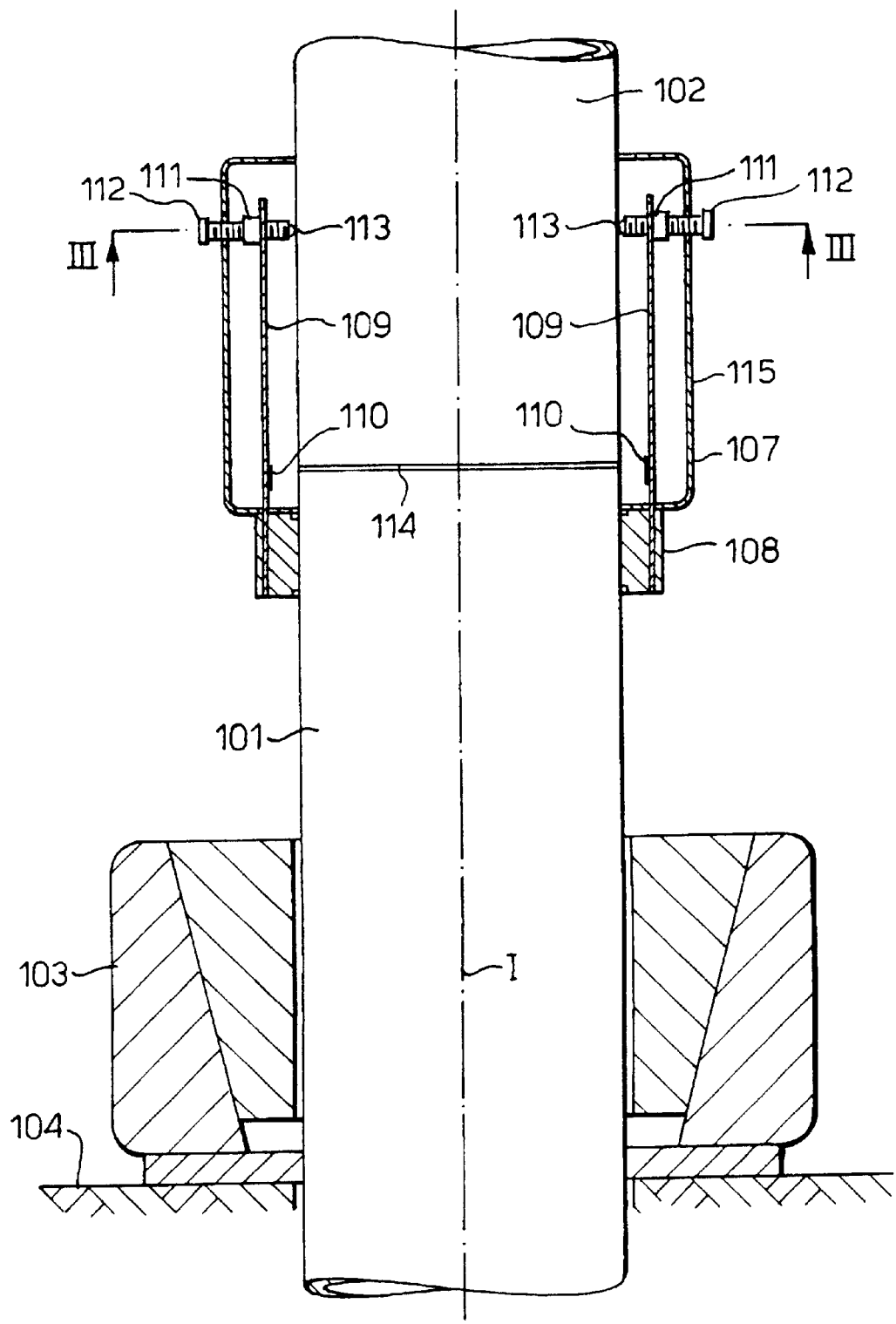
FIG. 1 is a view, partly in elevation and partly in section, of a joint about to be tested using one embodiment of an apparatus in accordance with the present invention.

The method of the present invention provides a means for testing a joint formed by bonding of two tubulars. Testing may take place directly on the rig floor, when one of the tubulars is being held in the slips.

The tubulars to be tested are bonded together; i.e., an end of a first tubular is bonded to an end of a second tubular and the bonded connection forms a joint therein between. In order to test the joint by the method of the inventions, one of the tubulars is held, for example in a set of slips. A force is then applied to the second tubular relative to the first tubular. When the force is removed, the final position of the second tubular is compared to the starting position. The preferred way of doing this comparison is by use of one or more sensors mounted remote from the joint between the two tubulars.

If the joint is correctly made then the final position of the second tubular should be substantially identical to its initial position. In this connection it is not intended that the force applied in step (c) should cause any permanent deformation, i.e. the force should not exceed the elastic limit of the tubular.

The force is preferably applied so that the second tubular will move relative to the first tubular in more than one direction.

Advantageously, the force is applied so that the center of the second tubular will move in substantially a circle around the longitudinal axis of the first tubular.

It is intended that the method of the invention will normally be performed during the running of a string of tubulars and accordingly the first tubular will normally be secured in the slips while the second tubular is moved relative thereto.

The movement may conveniently be performed by applying a force to the second tubular at or close to the upper extremity thereof.

If the sensor(s) are to be disposed close to the joint they can conveniently be mounted on the slips or on the first tubular member itself. However, if they are to be mounted adjacent the top of the second tubular they may conveniently be incorporated in the same device which is used to apply the force to the second tubular. For some purposes it may be desirable to incorporate sensor(s) at both levels.

It will be appreciated that tubulars are often run in extremely inclement conditions which can include high winds, driving rain, snow and heavy seas. All these factors can make it extremely difficult to determine whether the second tubular has returned to its original position or whether it has returned to a different position. This problem can conveniently be reduced by using light beams, particularly laser light beams, as a reference. In one embodiment a plurality of laser light beam sources can be mounted on a collar attached to the first tubular and directed upwardly onto a target mounted on the top of the second tubular. Initially after the joint is made the lasers are activated to burn small holes in the target. After the second tubular has been deflected and the force has been removed the lasers are re-activated. If the difference in the positions of the holes created before and after the test exceeds a predetermined amount based on the length and diameter of the pipe and the prevailing conditions, the tubulars must be cut above and below the joint and the joint re-made.

It is primarily intended that the force applied in step (c) will only displace the second tubular in a plane substantially perpendicular to the longitudinal axis of the first tubular since this will apply tensile forces to one part of the joint and compressive forces to the opposite part. Furthermore, substantially the entire length of the second tubular can be used as a lever. However, it is still possible that a tensile test could be carried out by simply applying an upward force to the second tubular to displace it upwardly relative to the first tubular, removing the upward force and checking to see whether the second tubular returns to its original position.

The present invention also provides an apparatus for testing the joint formed by bonding of two tubulars. The apparatus comprises a fixing device to hold a first tubular and a head to grip a second tubular. A sensor is included remote to the joint between the tubulars. The sensor is positioned to be responsive to the position of the second tubular. There is a means to move the head to displace the second tubular relative to the first tubular, and there is a means to allow the head to move to a position dictated by the second tubular during and after the test.

Preferably, the sensor is responsive to the position of the head.

The preferred apparatus may conveniently be made by modifying a conventional stabbing guide. In particular, stabbing guides are designed to grip an upper tubular and move it into alignment with a tubular in the slips prior to stabbing. The essential difference with the preferred apparatus of the present invention is that the stabbing guide is provided with one or more sensors arranged to provide signal(s) relating to the position of the head. In this connection, it should be noted that it is not vital that the sensors give the absolute position of the head, only that they indicate the difference in position before and after the test.

It is observed that various non-destructive techniques for testing materials such as beams, lumber and timber under the action of bending moments are known and disclosed in for example UK patent specifications No. 1202929, 1018726 and 1015222.

The invention will now be described with reference to the Figures.

Referring to FIG. 1 of the drawings there is shown a first tubular 101 which is joined to a second tubular 102 by an amorphous or other bonding process. The result joint is shown at 114.

The first tubular 101 is held fast in a set of slips 103 which are supported by a rig floor 104.

Figure 5:
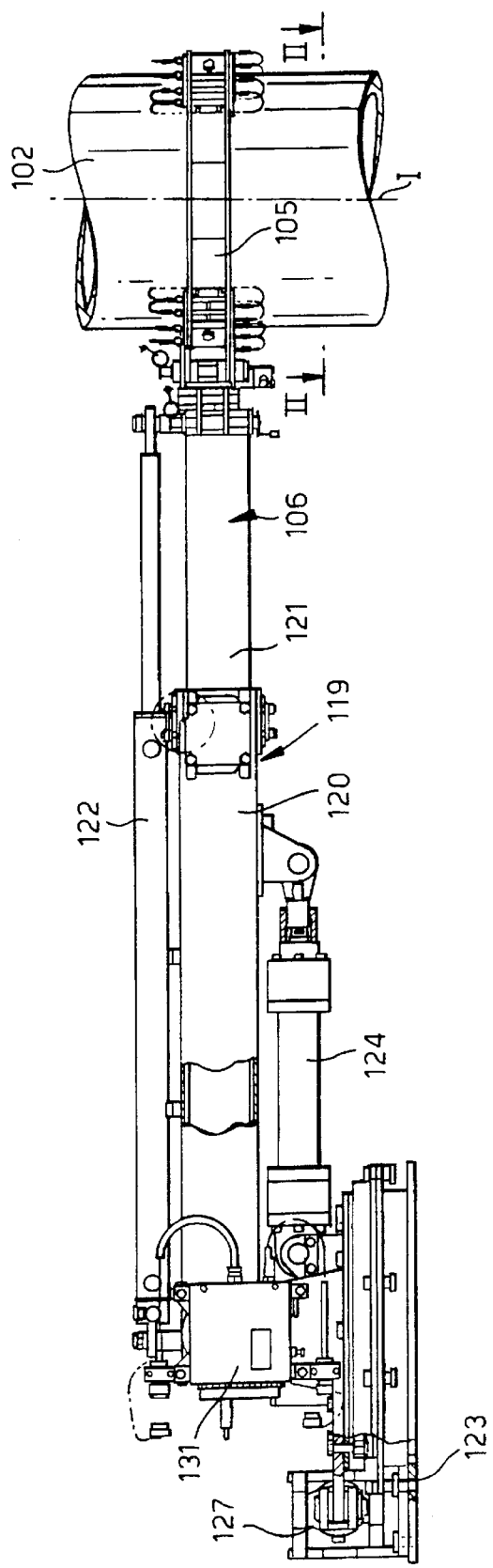
FIG. 5 is a side view of the positioning apparatus which is arranged at the top of the second tubular 102 shown in FIG. 1.
Figure 6:
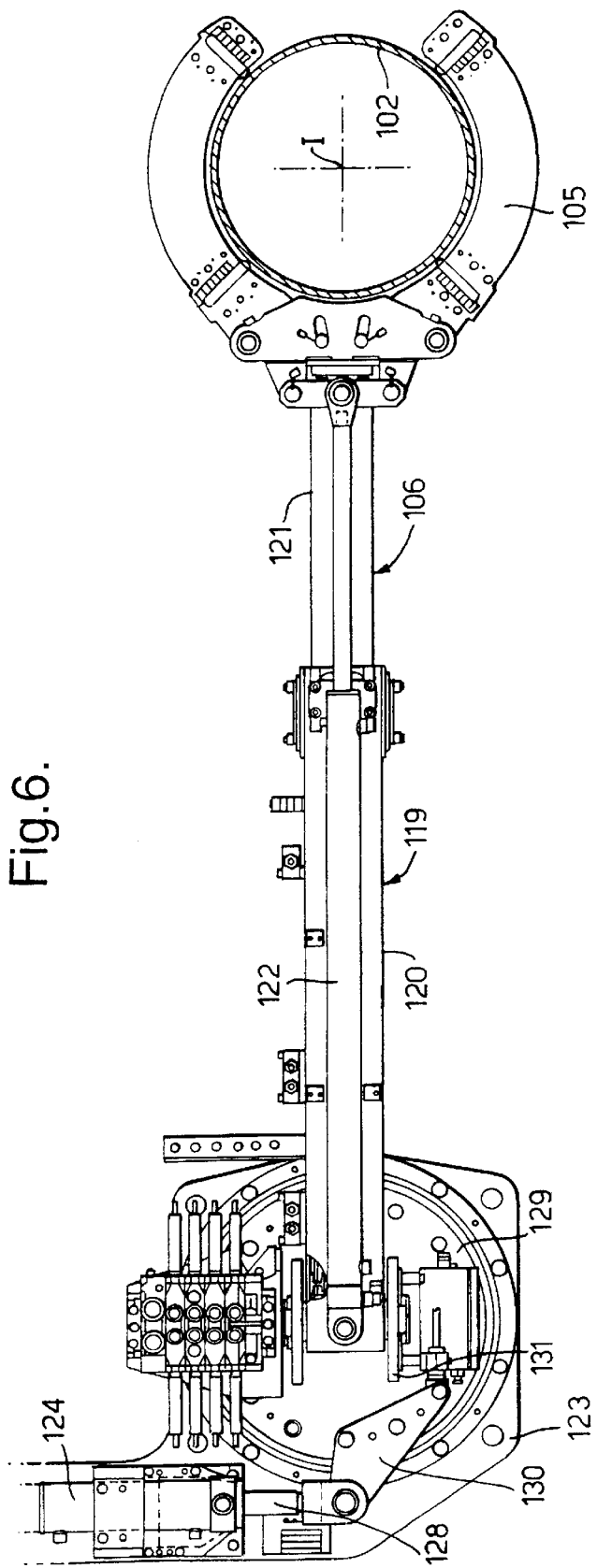
FIG. 6 is a plan view of the positioning apparatus shown in FIG. 5.

The upper portion of the second tubular 102 is located in a head 105 of a positioning device 106 as shown in FIG. 5 and 6.

At the start of the test a sensing apparatus 107 is mounted on the first tubular 101 via a two piece clamp 108 which has two halves which are hinged to one another and are connected circumjacent the first tubular 101. As shown in FIG. 3 six flexible arms 109 rise upwardly from the two piece clamp 108. A strain gauge 110 is secured to each flexible arm 109 as shown. A nut 111 is welded to the top of each flexible arm 109 and accommodates a bolt 112 having a rounded end 113 which presses against the second tubular 102 above the level of the amorphous bond 114 between the first tubular 101 and the second tubular 102.

The flexible arms 109 are protected by a housing 115.

In use, after the two piece clamp 108 has been secured to the first tubular 101 a quick check is carried out to ensure that the rounded ends 113 of the bolts 112 are bearing against the second tubular 102. This can conveniently be checked by checking that there is some signal from each of the strain gauges 110 indicating a state of tension. Although each of the strain gauges should be indicating a similar state of tension identity is not necessary. However, each of the readings are recorded.

The positioning device 106 shown in FIG. 5 and 6, which is typically about 10 m above the rig floor 104, is then actuated to displace the top of the second tubular 102 relative to the first tubular 101.

Figure 2:
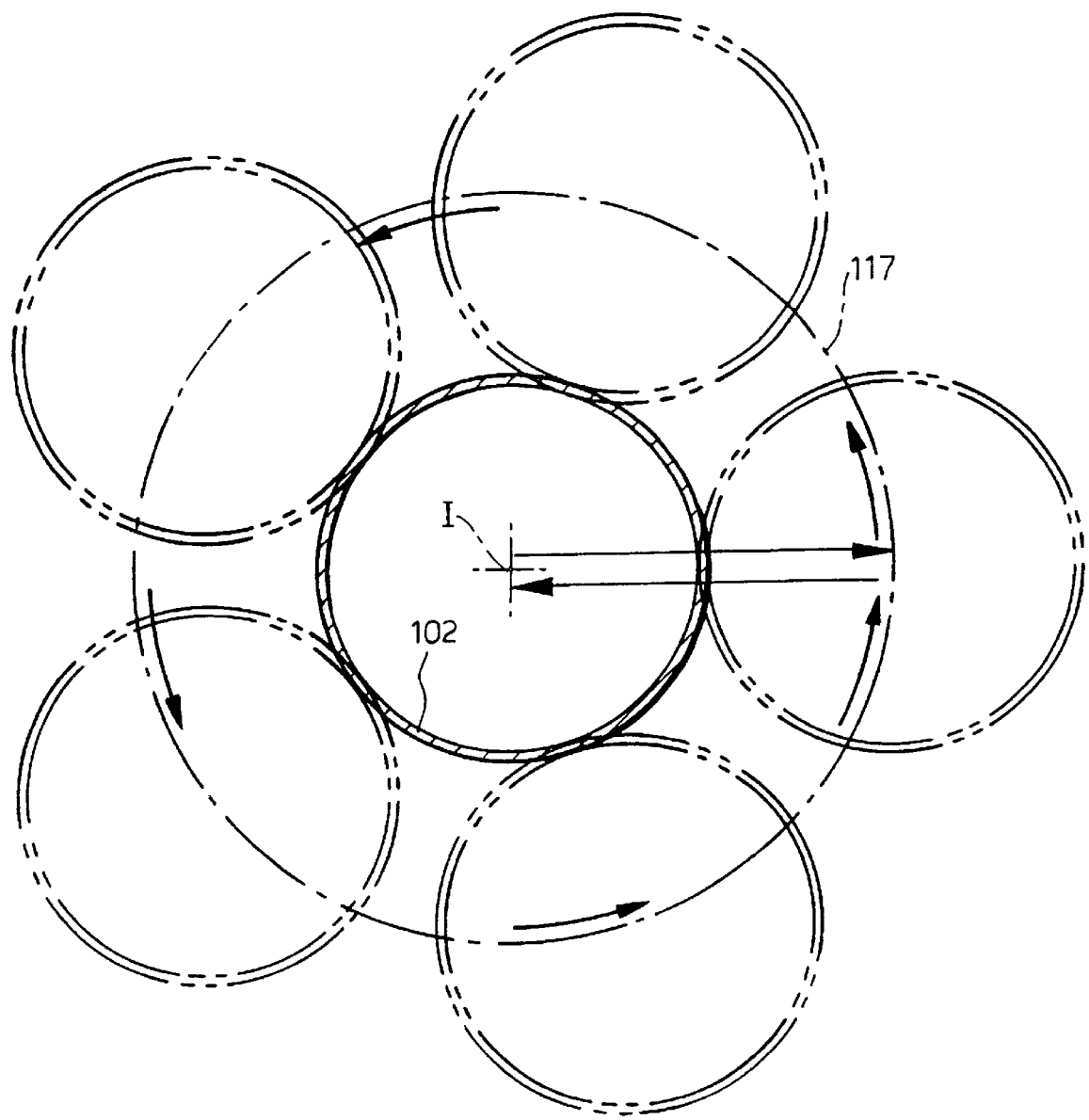
FIG. 2 is a section taken on line II–II of FIG. 5 showing the path of the second tubular during the test.

Referring now to FIG. 2, the second tubular 102 initially occupies a position which is substantially co-axial with the longitudinal axis I of the first tubular 101 (the first tubular is not shown in FIG. 2). At the start of the test the second tubular 102 occupies the position shown in full lines in FIG. 2. As the test progresses the positioning device 106 (not shown in FIG. 2) is actuated to move the top of the second tubular 102 so that the locus of its center moves along path 117.

When the top of the second tubular 102 has moved through a complete circle the positioning device 106 is deactivated. The resilience of the joint urges the second tubular 102 back towards its original position.

When the second tubular 102 has settled the readings on the strain gauges 110 are taken and compared with the original signals. If the signals are identical or substantially identical then the joint is totally satisfactory. If, however, the signals indicate that the second tubular 102 has not returned to its initial position (or acceptably close thereto) the joint should be cut out, remade and retested.

FIG. 4 shows an alternative sensing apparatus which is generally identified by the reference numeral 207. (Parts which have a function which are similar to the parts in FIG. 1 have been identified by similar members to those used in FIG. 1 except they are in the "200" series.) In this embodiment, the first tubular 201 is held fast in a set of slips 203 which are supported by the rig floor. As before, the upper portion on the second tubular 202 is located in the head 105 of a positioning device 106 as shown in FIG. 5 and FIG. 6. The essential difference between the sensing apparatus 207 and the sensing apparatus 107 shown in FIG. 1 is that the six flexible arms 209 are mounted on a ring 208 which is mounted fast on the slips 203 via a bridge 219. A strain gage 210 is secured to each flexible arm 209 as shown. A nut 211 is welded to the top of each flexible arm 209 and accommodates a bolt 212 having a rounded end 213 which presses against the second tubular 202 above the level of the amorphous bond 214 between the first tubular 201 and the second tubular 202.

Turning now to the positioning device 106, in the embodiment of FIGS. 5 and 6, this is conveniently formed by a conventional stabbing guide. In particular, the positioning device 106 comprises a telescopic beam 119 of rectangular cross-section having a first section 120 and a second section 121 which is attached to the head 105 and which can be extended and retracted by actuation of a hydraulic piston and cylinder 127.

The telescopic beam 119 is universally mounted on a base plate 123 which is fixed in the drilling derrick (not shown) about 10 m above the rig floor 104 shown in FIG. 1.

The telescopic beam 119 can be pivoted from a rest position (not shown) in which it extends substantially vertically to its operational position (as shown) by actuation of a lifting cylinder 124 which is pivotally mounted to the base plate 123 at support 125 and to the first section 120 at support 125.

The telescopic beam 119 can also be pivoted horizontally by a pivoting cylinder 127 which is mounted on the base plate 123. The pivoting cylinder 127 has a piston 128 which is attached to a rotor 129 which is rotatably mounted on the base plate 123 via a triangular connecting plate 130. When the piston 128 is extended the rotor 129 pivots anti-clockwise on the plate 123 (as viewed in FIG. 6) and when the piston 128 is retracted the rotor 129 pivots clockwise on the base plate 123. This movement is transmitted to the telescopic beam 119 via a support arrangement 131 which is mounted on the rotor 129. It will be appreciated that by extending and retracting the telescopic beam 119 while extending and retracting the piston 128 the second tubular 102 can be deflected in whatever tortuous path is required, the circle shown in FIG. 2 being considered particularly appropriate.

In the embodiments thus far described with reference to the drawings the sensing apparatus 107, 207 is disposed on or adjacent to the set of slips 103. This is not mandatory and the sensing apparatus could be located at a higher elevation as an alternative to (or in addition to) the aforesaid positions.

A particularly advantageous arrangement is to include the sensing apparatus in the positioning device 106.

This arrangement requires that the positioning device 106 includes a position sensing apparatus. In particular, the hydraulic piston and cylinder 122 will then incorporate a linear transducer such as made by Rota Engineering Limited of Bury, Manchester, England. Similarly, the piston 128 then incorporates a linear transducer. The two linear transducers are arranged to send signals indicative of the length of the telescopic beam 119 and the extension of the piston 128. These signals in turn specify the position of the head 105 in the horizontal plane.

While the signals from the linear transducers are primarily intended to provide information as to whether the position of the top of the second tubular 102 is the same before and after the displacement test the linear transducers can also be used to provide feedback signals to the computer which may be used to control the motion of the head 205 during the test itself.

While it will be appreciated that the implementation of the present invention does not present major technical problems in normal conditions it must be borne in mind that many oil and gas wells are drilled in unstable condition. Heavy seas, high winds and driving snow make even the most stable rig floors and tubular strings sway.

In order to help compensate for these forces the readings from each of the various sensors should be taken and averaged over a period of time both before and after the test and the results compared to see whether any deviation is outside a statistically acceptable limit.

When the sensing apparatus is placed in close proximity to the joint being tested the external effects are relatively small. However, it is also difficult to detect a failure of the second tubular 102 to return to its initial position after the test.

In contrast, it is comparatively easy to detect a failure of the second tubular 202 to return to its initial position when the sensing apparatus is mounted high in the derrick. However, in inclement conditions the derrick itself can move relative to the rig floor and these cause the positioning device 206 to sway. In order to help reduce this problem a beam of laser light mounted on, for example the slips, may be beamed upwardly to an array of photocells fast with the base plate 223 of the positioning device 206. The readings from the photocells can be used to compensate for any change in position between the slips and the positioning device.

A very simple system for checking alignment involves the use of a plurality of upwardly facing lasers which are mounted on the slips or on a collar attached to the first tubular 101 and a target mounted circumjacent the second tubular 102 adjacent the top thereof.

Prior to the test the lasers are activated to mark the target. After the test the lasers are re-activated to again mark the target. The target is then examined to see whether any difference in position is outside an acceptable limit taking into account the prevailing conditions.

What is claimed is:

1. A method of testing a joint formed by bonding of two tubulars, which method comprises the steps of:

a) providing a first tubular and a second tubular, wherein an end of the first tubular is bonded to an end of the second tubular to form a joint therein between;

b) holding said first tubular;

c) applying a force to displace said second tubular relative to said first tubular, wherein said displacement takes place predominately in a circular direction relative to said first tubular;

d) removing said force; and e) comparing the final position of said second tubular with the position which it occupied prior to step (c) by means of a sensor mounted remote from said joint, to determine if said joint between the tubulars is correctly made.

2. A method according to claim 1, wherein application of said force of step (c) results in said second tubular moving in-more than one direction relative to said first tubular.

3. A method according to claim 2, wherein application of said force results in the center of the second tubular moving in substantially a circle around the longitudinal axis of said first tubular.

4. A method according to claim 1, including the steps of holding said first tubular in a set of slips.

5. A method according to claim 1, further comprising applying said force of step (c) to the upper extremity of said second tubular or close thereto such that said upper extremity is urged to make an orbital movement relative to the longitudinal axis of the first tubular.

6. A method according to claim 1, wherein said sensor is mounted on said first tubular.

7. A method according to claim 6, wherein said sensor is incorporated in a device which is used to displace said second tubular relative to said first tubular.

8. An apparatus for testing a joint formed by bonding of two tubulars, which apparatus comprises:

a) a fixing device to hold a first tubular;

b) a head to grip a second tubular, an end of, said second tubular connected to an end of said first tubular to form a joint;

c) a sensor remote to said joint, said sensor is responsive to the position of said second tubular to be capable of determining if said joint is correctly made;

d) means to move said head to displace said second tubular in a circular direction relative to said first tubular; and e) means to allow said head to move to a position dictated by said second tubular.

9. An apparatus as claimed in claim 8 wherein said sensor is responsive to the position of said head.

10. An apparatus as claimed in claim 9, wherein said sensor is responsive to the position of said head in a generally horizontal plane.

* * * * *